(12) United States Patent
Kelly et al.

(10) Patent No.: US 12,232,720 B2
(45) Date of Patent: *Feb. 25, 2025

(54) SYSTEMS FOR SOFT TISSUE REPAIR

(71) Applicant: Howmedica Osteonics Corp., Mahwah, NJ (US)

(72) Inventors: William Thomas Kelly, White Plains, NY (US); Manoj Kumar Singh, Mahwah, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 293 days.

This patent is subject to a terminal disclaimer.

(21) Appl. No.: 17/699,559

(22) Filed: Mar. 21, 2022

(65) Prior Publication Data

US 2022/0211365 A1    Jul. 7, 2022

Related U.S. Application Data

(63) Continuation of application No. 16/219,263, filed on Dec. 13, 2018, now Pat. No. 11,284,879.

(51) Int. Cl.
| | |
|---|---|
| *A61B 17/04* | (2006.01) |
| *A61B 17/06* | (2006.01) |
| *A61B 17/11* | (2006.01) |
| *A61B 17/17* | (2006.01) |

(52) U.S. Cl.
CPC ...... *A61B 17/0469* (2013.01); *A61B 17/0401* (2013.01); *A61B 17/0482* (2013.01); *A61B 17/06066* (2013.01); *A61B 2017/0464* (2013.01); *A61B 2017/0472* (2013.01); *A61B 17/0483* (2013.01); *A61B 17/1146* (2013.01); *A61B 17/1714* (2013.01)

(58) Field of Classification Search
None
See application file for complete search history.

(56) References Cited

U.S. PATENT DOCUMENTS

| | | |
|---|---|---|
| 1,577,054 A | 3/1926 | Berkmann |
| 2,264,679 A | 12/1941 | Ravel |
| 4,971,075 A | 11/1990 | Lee |

(Continued)

FOREIGN PATENT DOCUMENTS

| | | |
|---|---|---|
| WO | 2014092863 A1 | 6/2014 |
| WO | 2018119459 A1 | 6/2018 |

OTHER PUBLICATIONS

Rush et al., U.S. Appl. No. 61/349,025, filed May 27, 2012, titled "Apparatus and Methods for Achilles Tendon Repair".

(Continued)

*Primary Examiner* — Shaun L David
(74) *Attorney, Agent, or Firm* — Lerner David LLP (57) ABSTRACT

A tissue repair apparatus includes a housing, a rotatable shaft at least partially disposed within the housing, and first and second curved needles coupled to the shaft. The housing defines a gap between a first edge of the housing and a second edge of the housing, the gap adapted to receive tissue. The first and second needles curved needles being articulable within the housing from a delivery position, at which the first and second needles are spaced from the gap, to a deployed position, at which the first and second needles extend through the gap. Actuation of the shaft simultaneously articulates the first and second needles and the first needle enters the gap before the second needle enters the gap.

20 Claims, 8 Drawing Sheets

(56) References Cited

U.S. PATENT DOCUMENTS

| | | | |
|---|---|---|---|
| 5,397,325 A | 3/1995 | Della Badia et al. |
| 5,458,609 A | 10/1995 | Gordon et al. |
| 5,653,718 A | 8/1997 | Yoon |
| 5,766,234 A | 6/1998 | Chen et al. |
| 5,797,927 A | 8/1998 | Yoon |
| 5,797,928 A | 8/1998 | Kogasaka |
| RE36,020 E | 12/1998 | Moore et al. |
| 5,843,126 A | 12/1998 | Jameel |
| 5,947,983 A | 9/1999 | Solar et al. |
| 5,980,538 A | 11/1999 | Fuchs et al. |
| 6,117,144 A | 9/2000 | Nobles et al. |
| 6,136,010 A | 10/2000 | Modesitt et al. |
| 6,322,571 B1 | 11/2001 | Adams |
| 6,475,135 B1 | 11/2002 | Levy |
| 6,533,795 B1 | 3/2003 | Tran et al. |
| 6,551,330 B1 | 4/2003 | Bain et al. |
| 6,613,058 B1 | 9/2003 | Goldin |
| 6,663,633 B1 | 12/2003 | Pierson, III |
| 6,743,241 B2 | 6/2004 | Kerr |
| 6,746,456 B2 | 6/2004 | Xiao |
| 6,921,408 B2 | 7/2005 | Sauer |
| 6,964,668 B2 | 11/2005 | Modesitt et al. |
| 7,001,400 B1 | 2/2006 | Modesitt et al. |
| 7,235,087 B2 | 6/2007 | Modesitt et al. |
| 7,445,626 B2 | 11/2008 | Songer et al. |
| 7,544,199 B2 | 6/2009 | Bain et al. |
| 7,585,305 B2 | 9/2009 | Dreyfuss |
| 7,628,796 B2 | 12/2009 | Shelton, IV et al. |
| 7,758,597 B1 | 7/2010 | Tran et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,842,047 B2 | 11/2010 | Modesitt et al. |
| 7,846,169 B2 | 12/2010 | Shelton, IV et al. |
| 7,846,170 B2 | 12/2010 | Modesitt et al. |
| 7,887,554 B2 | 2/2011 | Stokes et al. |
| 7,976,553 B2 | 7/2011 | Shelton, IV et al. |
| 8,038,688 B2 | 10/2011 | Modesitt et al. |
| 8,048,092 B2 | 11/2011 | Modesitt et al. |
| 8,057,491 B2 | 11/2011 | Modesitt et al. |
| 8,123,102 B2 | 2/2012 | Manzo |
| 8,137,364 B2 | 3/2012 | Zung et al. |
| 8,142,448 B2 | 3/2012 | Pasricha et al. |
| 8,172,860 B2 | 5/2012 | Zung et al. |
| 8,287,557 B2 | 10/2012 | To et al. |
| 8,403,947 B2 | 3/2013 | Ochiai |
| 8,500,756 B2 | 8/2013 | Papa et al. |
| 8,641,728 B2 | 2/2014 | Stokes et al. |
| 8,663,248 B2 | 3/2014 | Zung et al. |
| 8,936,611 B2 | 1/2015 | Rush et al. |
| 9,078,633 B2 | 7/2015 | Belson et al. |
| 9,173,654 B2 | 11/2015 | Rush et al. |
| 9,289,205 B2 | 3/2016 | Rohl et al. |
| 9,999,422 B2 | 6/2018 | Rush et al. |
| 2002/0198542 A1 | 12/2002 | Yamamoto et al. |
| 2003/0167063 A1 | 9/2003 | Kerr |
| 2003/0181925 A1 | 9/2003 | Bain et al. |
| 2003/0236535 A1 | 12/2003 | Onuki et al. |
| 2005/0055038 A1 | 3/2005 | Kelleher et al. |
| 2006/0282097 A1 | 12/2006 | Ortiz et al. |
| 2007/0198037 A1 | 8/2007 | Deland |
| 2009/0138029 A1 | 5/2009 | Saliman et al. |
| 2009/0318958 A1 | 12/2009 | Ochiai |
| 2010/0160934 A1 | 6/2010 | Kelleher et al. |
| 2011/0015654 A1 | 1/2011 | Tsuang et al. |
| 2011/0313454 A1 | 12/2011 | Rush et al. |
| 2012/0035654 A1 | 2/2012 | Belson |
| 2012/0239053 A1 | 9/2012 | Belliard et al. |
| 2013/0317544 A1 | 11/2013 | Ferguson et al. |
| 2014/0163583 A1 | 6/2014 | Rush et al. |
| 2014/0163584 A1 | 6/2014 | Rohl et al. |
| 2014/0358166 A1 | 12/2014 | Kelleher et al. |
| 2015/0127026 A1 | 5/2015 | Rush et al. |
| 2017/0304099 A1 | 10/2017 | Keren et al. |

OTHER PUBLICATIONS

Extended European Search Report for Application No. EP19215219.7, dated Mar. 2, 2020, pp. 1-2.

SYSTEMS FOR SOFT TISSUE REPAIR

CROSS-REFERENCE TO RELATED APPLICATIONS

This application is a continuation of U.S Application No. 16/219,263, filed on Dec. 13, 2018, the disclosure of which is incorporated herein by reference.

BACKGROUND OF THE INVENTION

The present invention relates generally to medical devices and methods for repairing soft tissue. More particularly, the present invention relates to devices and methods for reattaching torn soft tissue ends such as a ruptured Achilles tendon in a minimally invasive manner.

Soft tissue damage, particularly a ruptured Achilles tendon, is often a debilitating event that necessitates surgery. Reattaching a ruptured Achilles tendon generally requires that the torn or ripped ends of the tendon be coapted by passing one or more sutures through each damaged end. Each of the torn ends may then be drawn towards one another by tightening the sutures to restore the connecting muscles and tendon to their original lengths.

Accessing the damaged tissue, however, generally requires relatively large incisions, or multiple smaller incisions, for effecting adequate purchase and sufficient suturing of the damaged tendon to ensure proper healing of the tendon. Nonetheless, relatively large incisions, or multiple incisions, increase the likelihood of infections and result in prolonged recovery periods.

Minimally invasive devices, which may be inserted through relatively smaller incisions, are generally limited in their application for repairing particular tissue regions. For instance, while minimally invasive devices may enable a surgeon to pass sutures through tissue, these instruments are often limited in their ability to pass multiple sutures through non-supported tissue structures in an efficacious manner. Moreover, many such devices are insufficient in supporting unsupported tissue structures such as a ruptured Achilles tendon during suturing.

Nevertheless, due to the complications of open surgical operations, minimally invasive tissue repair systems are of continued interest. Two such tissue repair systems, are disclosed in U.S. Pat. Nos. 8,936,611 and 9,289,205, each of which is assigned to Applicant and incorporated herein by reference in its entirety.

BRIEF SUMMARY OF THE INVENTION

In repairing damaged regions of tissue, the elongated housing disclosed herein may be introduced through a single incision to access damaged tissue such as a ruptured or torn Achilles tendon and to pass multiple sutures through the tendon. Thus, the tendon repair assembly may generally include a housing, a rotatable shaft at least partially disposed within the housing, and first and second curved needles. The housing defines a gap between a first edge of the housing and a second edge of the housing, the gap being adapted to receive tissue. The first and second curved needles are articulable within the housing from a delivery position, at which the first and second needles are spaced from the gap, to a deployed position, at which the first and second needles extend through the gap. Rotation of the shaft simultaneously articulates the first and second needles such that the first needle enters the gap before the second needle enters the gap.

A base end of the first needle and base end of the second needle are mounted on an outer surface of the rotatable shaft along an axis that extends parallel to a longitudinal axis of the rotatable shaft. The first and second needles and the rotatable shaft may be a single monolithic structure and the first needle may have a greater length than the second needle.

The first needle may include a first notch spaced a first distance from a piercing tip of the first needle and the second needle may include a second notch spaced a second distance from a piercing tip of the second needle such that the first distance is greater than the second distance. The first needle may define a suture channel along an outer portion of the first needle and the second needle may define a suture channel along an outer portion of the second needle.

The tissue repair apparatus may further include a suture having a first portion disposed in the suture channel of the first needle forming a first loop, and a second portion disposed in the suture channel of the second needle forming a second loop. The first needle may include a first notch spaced a first distance from a piercing tip of the first needle and the second needle may include a second notch spaced a second distance from a piercing tip of the second needle such that the first distance is greater than the second distance and the first portion of the suture spans the first notch and the second portion of the suture spans the second notch.

The system may further include a stylet adapted to carry a cinching suture. The stylet may be slidably disposed within a locking channel defined within a wall of the housing. The first needle may include a first notch spaced a first distance from a piercing tip of the first needle and the second needle may include a second notch spaced a second distance from a piercing tip of the second needle, the first distance being greater than the second distance, such that when the first needle and the second needle are in the deployed position, the first notch and the second notch are longitudinally aligned with one another along the locking channel.

In another embodiment, a tissue repair apparatus includes a housing defining a gap between a first edge of the housing and a second edge of the housing, a rotatable shaft at least partially disposed within the housing, and a plurality of curved needles connected to the rotatable shaft. The gap is adapted to receive tissue. The plurality of curved needles is articulable from a delivery position in which the plurality of curved needles is spaced from the gap to a deployed position in which the plurality of curved needles extends through the gap. Rotation of the shaft simultaneously articulates the plurality of curved needles and each one of the plurality of curved needles enters the gap in a sequential order.

When the plurality of needles are in the delivery position, each one of the plurality of needles is at least partially positioned within a wall of the housing and on a single side of the gap. A base end of each of the plurality of needles may by be mounted on an outer surface of the rotatable shaft along an axis that extends parallel to a longitudinal axis of the rotatable shaft. The plurality of curved needles may include a first curved needle having a first arc length, a second curved needle having a second arc length, and a third curved needle having a third arc length such that the first arc length is longer than the second arc length and the second length is longer than the third arc length. Each one of the first curved needle, the second curved needle, and the third curved needle may define a suture channel along an outer radial edge of the needle.

The first curved needle may include a first notch spaced a first distance from a piercing tip of the first needle, the second curved needle may include a second notch spaced a second distance from a piercing tip of the second needle, and the third needle may include a third notch spaced a third distance from a piercing tip of the third needle such that the first distance is greater than the second distance and the second distance is greater than the third distance.

When the plurality of needles are in the deployed position, the first notch, the second notch, and the third notch are longitudinally aligned with one another along a locking channel provided within the housing.

The tissue repair apparatus may further include a stylet adapted to carry a cinching suture, the stylet being slidably disposed within the locking channel. In some instances, the locking channel may be at least partially disposed within a wall of the housing. The tissue repair apparatus may also include a contiguous suture having a first portion disposed in the suture channel of the first needle forming a first loop, a second portion disposed in the suture channel of the second needle forming a second loop, and a third portion disposed in the suture channel of the third needle forming a third loop.

A piercing end of at least one of the plurality of needles may include dual prongs and at least a portion of the suture channel may be provided between the prongs. Additionally, or alternatively, a piercing end of at least one of the plurality of needles may include a single prong. The single prong may be substantially triangular in shape and tapered from a first lateral side of the single prong to a second lateral side of the single prong.

In yet another embodiment, a method for repairing a tissue region includes positioning a portion of a ruptured or torn tendon tissue within a tissue receiving gap defined in a housing of a suture delivery assembly and simultaneously actuating first and second needles at least partially through the tissue receiving gap such that the first and second needles respectively pierce the ruptured or torn tendon tissue at first and second locations with the first needle entering the tissue receiving gap before the second needle enters the tissue receiving gap.

The first needle may define a first stylet clearance slot spaced a first distance from a piercing tip of the first needle and the second needle may define a second stylet clearance slot spaced a second distance from a piercing tip of the second needle, the first distance being greater than the second distance. When the first needle and the second needle are in a deployed position, the first stylet clearance slot and the second stylet clearance slot are longitudinally aligned with one another along a locking channel of the housing.

The method may further include the step of passing a suture through the ruptured or torn tendon tissue at the first location and the second location and advancing a stylet carrying a cinching suture in a longitudinal direction through the suture delivery assembly and through the first stylet clearance slot and the second stylet clearance slot.

Introduction of the suture delivery assembly may include introducing the suture delivery assembly through a single incision along a posterior region of a leg. After the tissue region has been repaired, the first needle and the second needle may be retracted and the suture delivery assembly may be withdrawn from the incision. In some instances, the ruptured or torn tendon tissue may be the Achilles tendon.

DETAILED DESCRIPTION

Figure 1A:
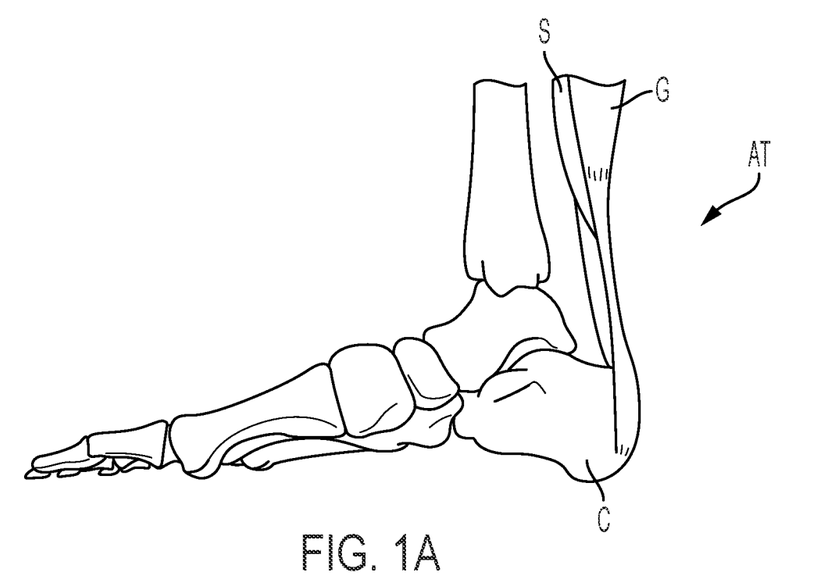
FIG. 1A is a schematic representation of a human ankle and foot including the Achilles tendon.

FIG. 1A is a schematic representation of an Achilles tendon AT, the ropelike band of fibrous tissue located in the posterior region of the ankle that couples the plantaris (not shown), gastrocnemius G and soleus muscles S to the calcaneus bone C. These muscles, acting via the Achilles tendon, cause plantar flexion and dorsiflexion of the foot at the ankle and flexion at the knee.

Figure 1B:
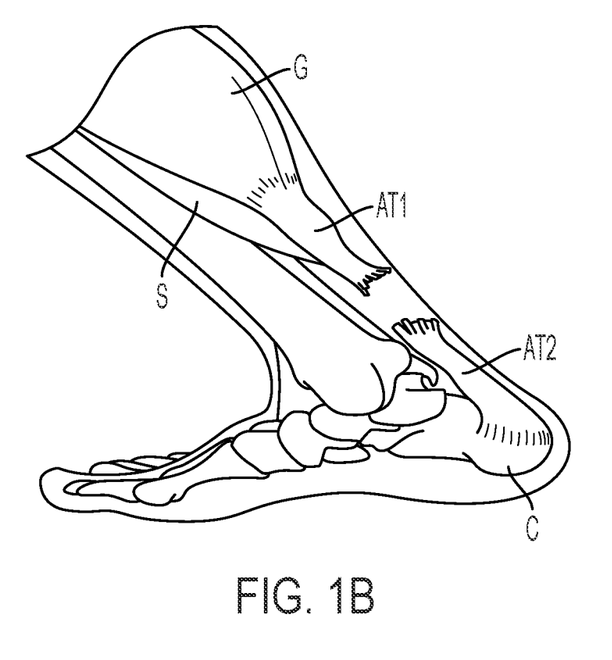
FIG. 1B is a schematic representation of the human ankle and foot and illustrating a ruptured Achilles tendon.

As a result of direct trauma to the tendon or injury to the lower leg, foot, or ankle, the Achilles tendon may rupture, as shown in FIG. 1B, when a sudden force is placed on the tendon that is greater than the tendon can endure. Once the Achilles tendon has ruptured or been severed into a first Achilles tendon portion AT1 and a second Achilles tendon portion AT2, flexion at the foot and knee is no longer possible, rendering basic functions of the foot, such as walking, incredibly difficult. As a result, a ruptured Achilles tendon often requires surgery to coaptate the severed ends of the tissue and restore proper function to the foot and ankle.

The devices and methods described herein are configured to suture the severed ends of the first and second Achilles tendon portions AT1, AT2 to one another in a minimally invasive manner. Although the devices and methods are described herein in connection with the repair of the Achilles tendon, it will be appreciated that these concepts may be equally applicable to the repair of other tendons or tissue regions.

Figure 2A:
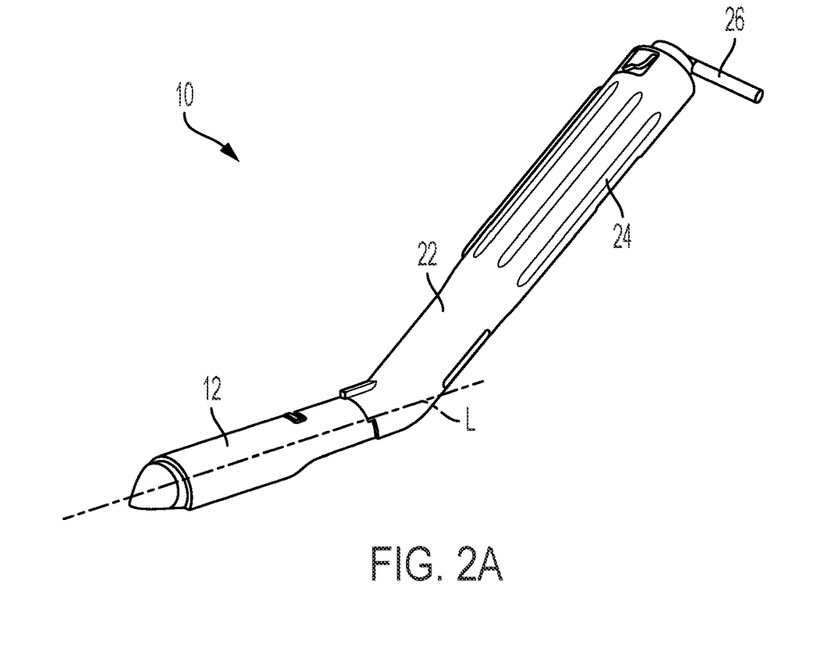
FIG. 2A is a front facing perspective view of a suture delivery device according to an embodiment of the present disclosure.
Figure 2B:
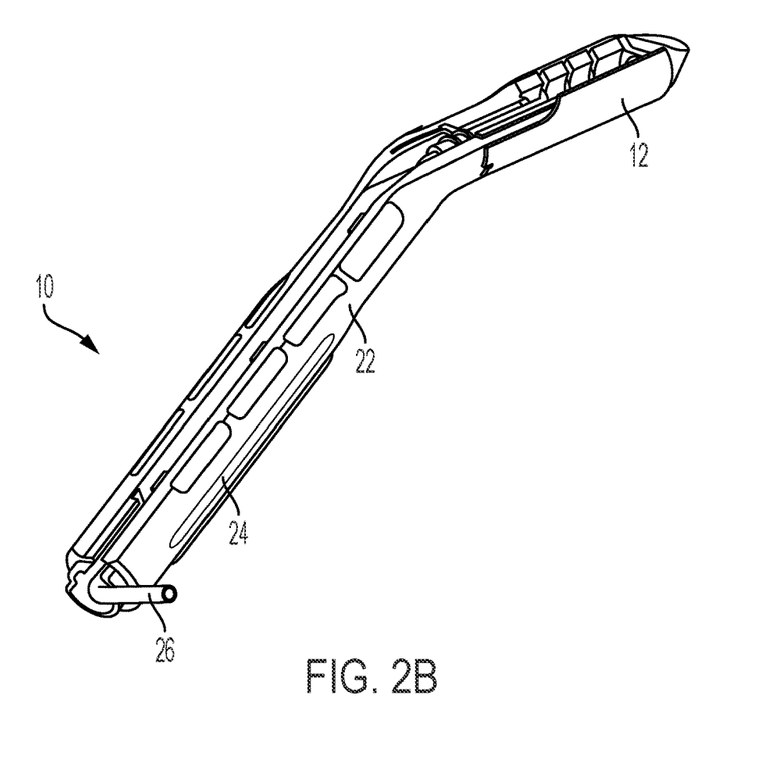
FIG. 2B is a rear facing perspective view of the suture delivery device of FIG. 2A.
Figure 2C:
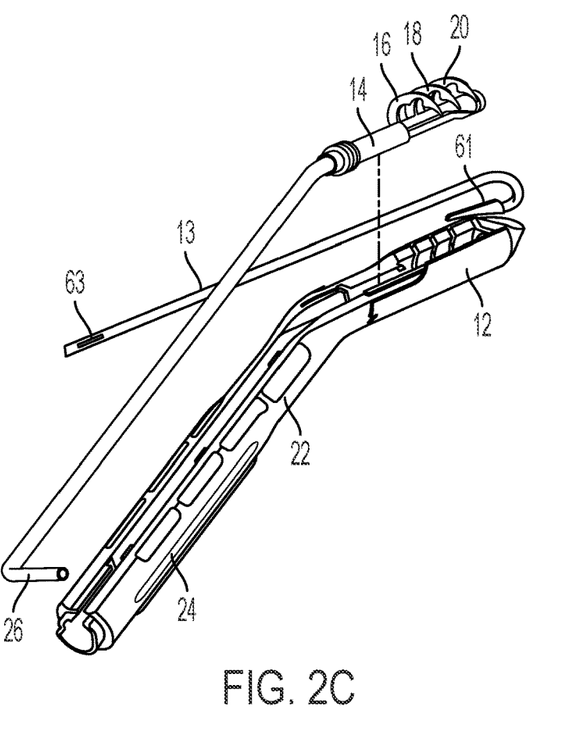
FIG. 2C is an exploded view of the suture delivery device of FIG. 2B.

A tissue repair device 10, as shown in FIGS. 2A-2C, includes a housing 12, a stylet 13, and an elongated shaft 14 having a plurality of needles 16, 18, 20 (collectively "needle assembly") disposed within and articulable through the housing.

Housing 12 includes a handle 22 having an ergonomically shaped grip 24 for manipulating tissue repair device 10. As shown, housing 12 and handle 22 are a monolithic component, however, it will be appreciated that the handle may also be connected to or otherwise coupled to the housing. Handle 22 is preferably angled about a longitudinal axis L of housing 12, for example, from about 30 degrees to about 90 degrees. This angled orientation allows the user to insert housing 12 through an incision in a posterior region of a patient's leg to access the Achilles tendon without interference from the patient's lower leg.

Handle 22 further includes actuator 26 for actuating rotation of shaft 14 and, in turn, articulating the needle assembly. Although actuator 26 is shown in FIGS. 2A-2C as a rotatable member extending generally perpendicular to handle 22, it will be appreciated that the actuator may alternatively be formed as a pressable button, a trigger, or any other mechanism known in the art configured to cause rotation of shaft 14.

Referring to FIG. 3A-3D, housing 12 is generally elongated in shape with a hollow interior for receiving a ruptured Achilles tendon. Housing 12 extends along longitudinal axis L from a proximal end 28 nearest handle 22 to an opposing distal end 30 and may be a thin metal tube that acts as a cover or stiffening component for the features described below.

The distal end 30 of housing 12 may be rounded or otherwise atraumatic in shape to prevent damage of surrounding tissues when the housing is introduced into the leg of a patient. Housing 12 may have a length of about 5.6 cm, although the housing may be lengthened or shortened as desired. Moreover, housing 12 may have a semi-circular cross-sectional shape ranging, for example, from between 1 to 2.5 cm in diameter. In other variations, the cross-sectional shape may be elliptical or another shape conducive for atraumatic insertion into the patient's body.

Housing 12 has an opening 32 extending along a bottom side 34 of the housing that allows a ruptured Achilles tendon to be inserted into the hollow interior. The bottom side 34 of housing 12 may be inwardly tapered to assist a user in sliding Achilles tendon portions AT1, AT2 into the hollow interior. Housing 12 further defines a shaft cavity 36 in which shaft 14 is rotatably secured.

Shaft cavity 36 divides the interior of housing 12 into a first side having a pre-deployment wall 38 and a second side having deployment wall 40 such that a gap 42 is formed therebetween. Gap 42 is defined by the inner most edges of the pre-deployment and deployment walls 38, 40. Both pre-deployment and deployment walls 38, 40 may be generally convex in shape relative to longitudinal axis L.

Figures 3A, 3B:
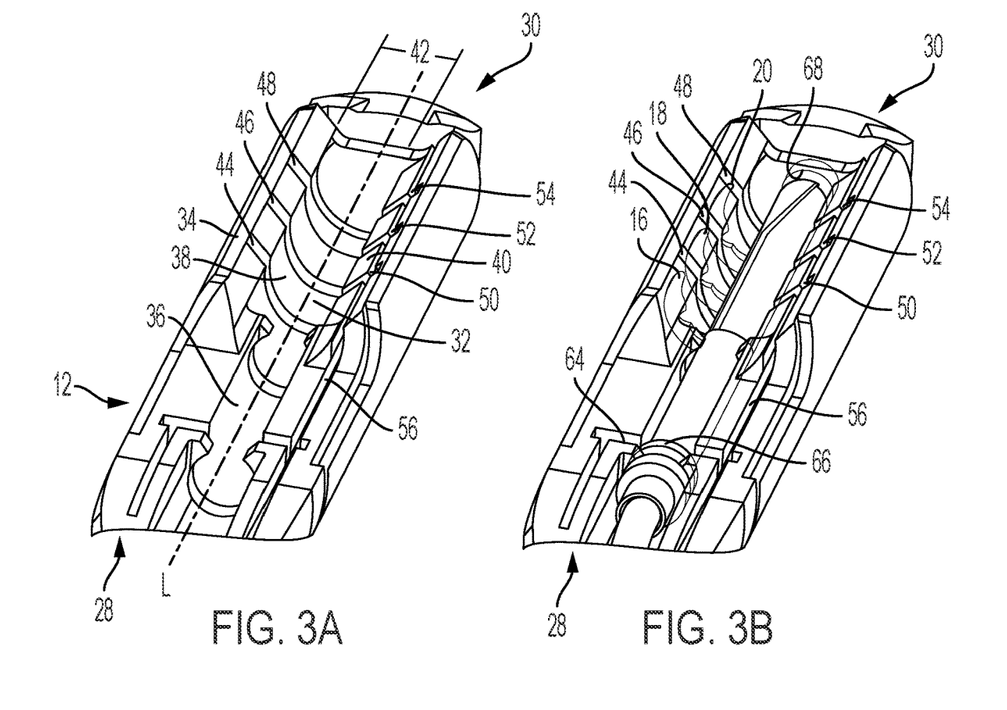
FIG. 3A is a bottom facing perspective view of a housing of the suture delivery device of FIG. 2B.
FIG. 3B is a bottom facing perspective view of the housing and needle assembly of FIG. 2B illustrating the needle assembly in a delivery position.

Pre-deployment wall 38 defines a plurality of needle recesses 44, 46, 48 in which needles 16, 18, 20 are respectively housed in a delivery position (e.g., before actuation). As shown in FIG. 3B, needle recesses 44, 46, 48 have a depth sufficient to completely conceal needles 16, 18, 20 behind an interior face of pre-deployment wall 38 such that the needles do not extend into gap 42 when the needle assembly is in the delivery position. Although illustrated with needle recesses 44, 46, 48, it will be appreciated that housing 12 may include any number of needles recesses including fewer than three recesses or more than three recesses such that the number of needle recesses correspond to the number of needles provided in the needle assembly.

Figures 3C, 3D:
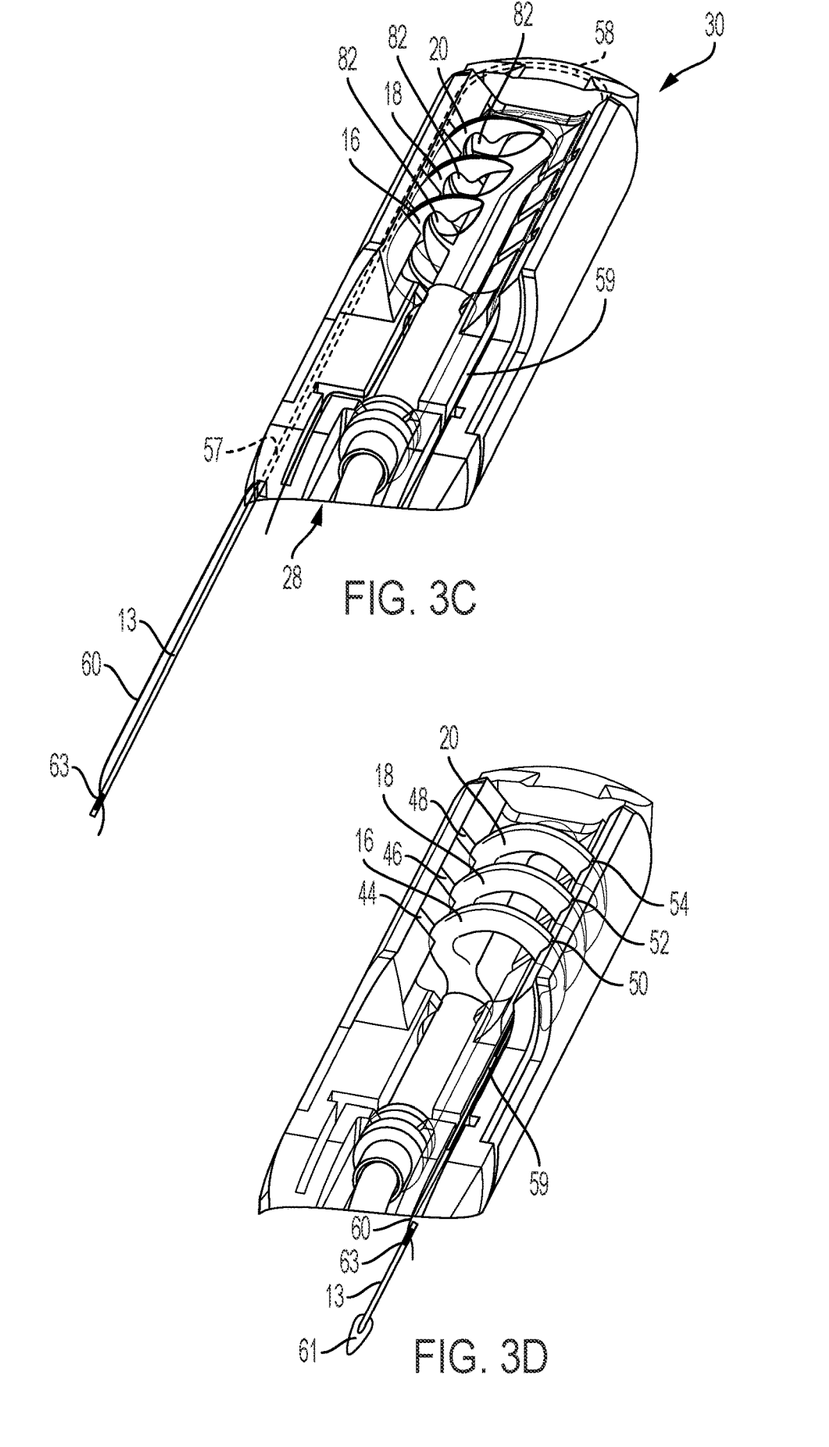
FIG. 3C is a bottom facing perspective view of the housing and needle assembly of FIG. 2B illustrating the needle assembly shortly after it has been actuated.
FIG. 3D a bottom facing perspective view of the housing and needle assembly of FIG. 2B illustrating the needle assembly in a deployed position.

Deployment wall 40 defines a plurality of needle receiving slots 50, 52, 54 that respectively oppose needle recesses 44, 46, 48 and receive needles 16, 18, 20 when the needle assembly is in a deployed position (e.g., after actuation) as shown in FIG. 3D.

Housing 12 also defines a stylet channel 56 that wraps around a perimeter of the housing. Stylet channel 56 is preferably concealed behind an interior face of pre-deployment wall 38 and an interior face of deployment wall 40 such that the stylet channel extends through needle receiving slots 50, 52, 54.

Referring to FIG. 3C, the portion of stylet channel 56 that extends from the proximal end 28 of housing 12 toward the distal end 30 of the housing and is located behind pre-deployment wall 38 is referred to herein as the loading portion 57. The portion of stylet channel 56 that extends from the distal end 30 of housing 12 toward the proximal end 28 of the housing and is located behind deployment wall 40 is referred to herein as the locking channel 59. The arcuate portion of stylet channel 56 that extends along the distal end 30 of housing 12 from loading portion 57 to locking channel 59 is referred to herein as the transition section 60.

As is shown in FIGS. 2C, 3C and 3D, stylet 13 may be an elongated, thin, flexible ribbon having a bullet-shaped tip 61, or guide runner, and an aperture 63 that acts as an eyelet for carrying a cinching suture 60. Stylet 13 may be pre-loaded (or loaded by a user before operation) into stylet channel 56 via loading portion 57 and positioned as shown in FIG. 3C, such that the tip is located at the distal end of locking channel 59. Thus, as will be explained hereinafter, as stylet 13 slides through locking channel 59, cinching suture 60 is passed through the locking channel and each one of needle receiving slots 50, 52, 54.

With specific reference to FIG. 3B, shaft cavity 36 may define a groove 64 that is adapted to receive a correspondingly shaped protrusion 66 provided on a proximal end of shaft 14, and a pocket 68 at the distal end 30 of housing 12 for rotatably securing the shaft within the shaft cavity.

Figure 4A:
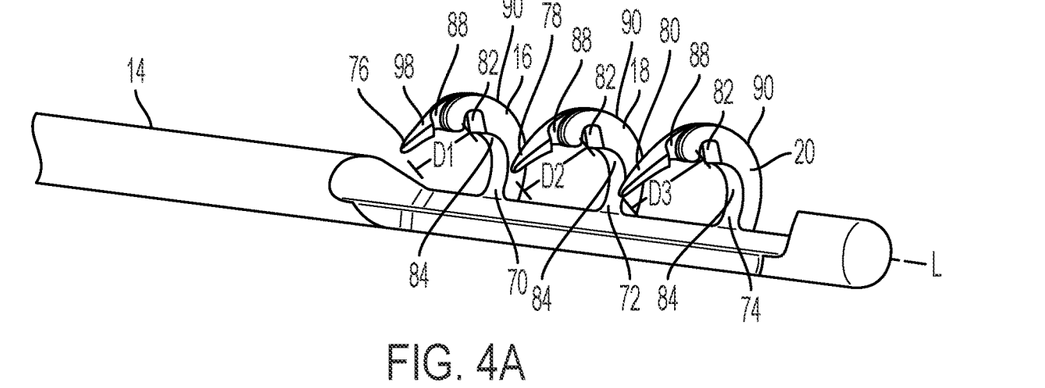
FIG. 4A is a perspective view of an exemplary needle assembly in which each needle has a single prong.
Figure 4B:
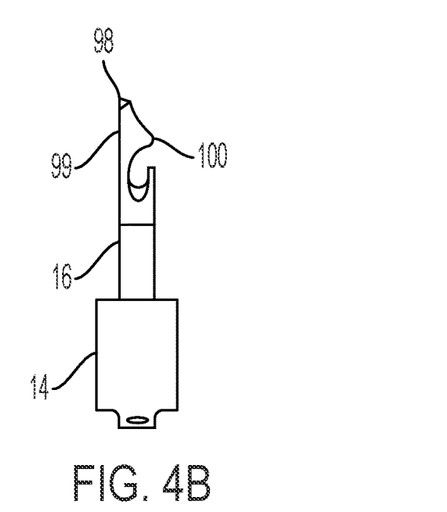
FIG. 4B is a front plan view of one of the needles shown in FIG. 4A.
Figure 4C:
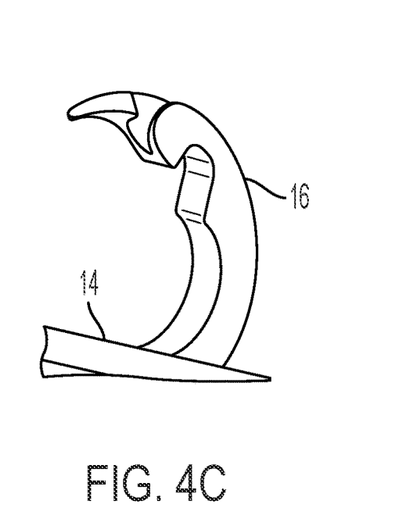
FIG. 4C is a perspective view of the needle shown in FIG. 4B.
Figure 4D:
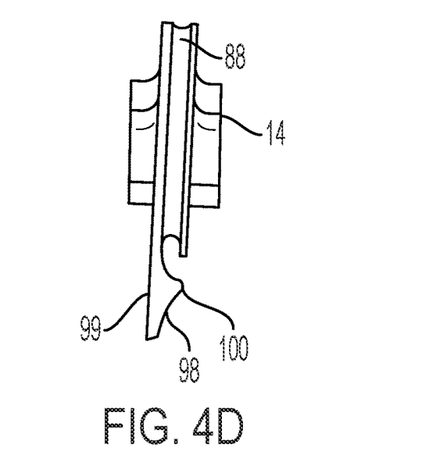
FIG. 4D is a top view of the needle shown in FIG. 4B.
Figure 5A:
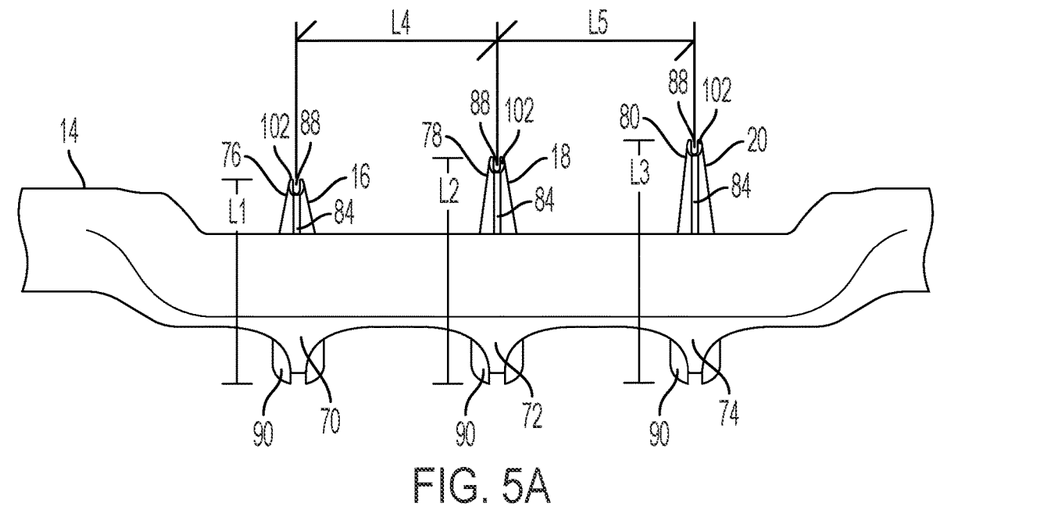
FIG. 5A is a bottom plan view of another exemplary needle assembly in which each needle has a double pronged tip.
Figure 5B:
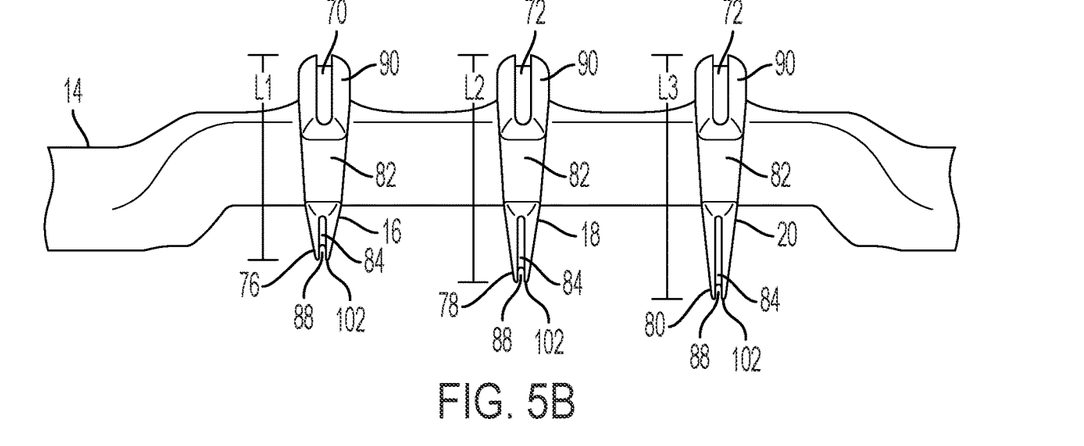
FIG. 5B is a bottom plan view of another exemplary needle assembly in which each needle has a double pronged tip.

As shown in FIGS. 4, 5A, and 5B, needles 16, 18, 20 may be integral with shaft 14 such that the needle assembly and the shaft are formed as a single monolithic piece. Alternatively, the needle assembly may be connected to or otherwise coupled to shaft 14 after formation of each component. Each one of needles 16, 18, 20 are curved or arcuate in shape and include base ends 70, 72, 74 extending from an outer surface of shaft 14 towards free ends or needle tips 76, 78, 80. The base ends 70, 72, 74 of needles 16, 18, 20 may be mounted on an outer surface of rotatable shaft 14 along an axis that extends parallel to a longitudinal axis of the rotatable shaft.

Needle 16 has a first arc length L1, needle 18 has a second arc length L2 that is greater than the first arc length of needle 16, and needle 20 has a third arc length L3 that is greater than the second arc length of needle 18. For example, L1 may be about 0.38 cm to about 0.43 cm, L2 may be about 0.43 cm to about 0.46 cm, and L3 may be about 0.47 cm to about 0.53 cm although other dimension are contemplated. In one embodiment, L1 is 0.41 cm, L2 is 0.45 cm, and L3 is 0.49 cm. In another embodiment, based on the arc length of the shortest needle, each successively larger needle can be about 10% longer. Moreover, needle 16 is spaced a first distance L4 from needle 18 and needle 18 is spaced a second distance L5 from needle 20. As is shown in FIG. 5A, the first distance L4 may be equal to the second distance L5, for example, L4 and L5 may be about 0.75 cm. However, in alternative embodiments, L4 may be less than, or greater than L5. In further embodiments, more than three needles can be provided, and the distance between adjacent needles at one end can be shorter than the distance between adjacent needles at the opposite end of the needle array. This can be useful where a more secure grip in the tissue is desired at an area closer to the tear, for example.

Each one of needles 16, 18, 20 may have an equal curvature, i.e. an equal radius of curvature about which they extend. Thus, when shaft 14 is rotated, each one of needles 16, 18, 20 simultaneously begins to articulate through housing 12 and needle tips 76, 78, 80 enter gap 42 in a sequential order (e.g., needle tip 80 enters the gap first, followed by needle tip 78, followed by the needle tip 76) as shown in FIG. 3C. As a result, the needle assembly provided herein is configured to sequentially pierce a tendon (as opposed to concurrently). As used herein, sequential order or sequentially means at least one of the needles enters the gap at a different time than at least one of the other needles. By spacing out the times at which needles 16, 18, 20 pierce the tendon, the impact forces that are exerted on the tendon are reduced and the risk of trauma is minimized.

As shown in FIGS. 3C, 4, and 5B a notch 82 is provided in each one of needles 16, 18, 20. Notches 82 may be provided in an inner circumferential edge 84 (FIG. 4) or an outer circumferential edge 90 (FIG. 5B) of needles 16, 18, 20 and may be provided an equal distance from base members 70, 72, 74. In other words, the notch of needle 16 is spaced a first distance D1 from needle tip 76, the notch of needle 18 is spaced a second distance D2 from needle tip 78, the second distance being greater than the first distance, and the notch of needle 20 is spaced a third distance D3 from needle tip 80, the third distance being greater than the second distance. This spacing ensures that each one of the notches 82 are aligned with one another along an axis that extends parallel to the longitudinal axis L of housing 12 throughout articulation of the needle assembly. Thus, when needles 16, 18, 20 are in the deployed position (FIG. 3D) and received within needle receiving slots 50, 52, 54, each one of the notches 82 are aligned along locking channel 59 such that stylet 13 may be passed through the notches.

Each one of needles 16, 18, 20 also defines a suture channel 88 formed along an outer surface of the needle, for example, along a length of the needle's outer circumferential edge 90. A first suture S1, which may be a single continuous suture or may be formed of multiple sutures tied to one another, is wrapped around the needle assembly as follows.

Figure 6A:
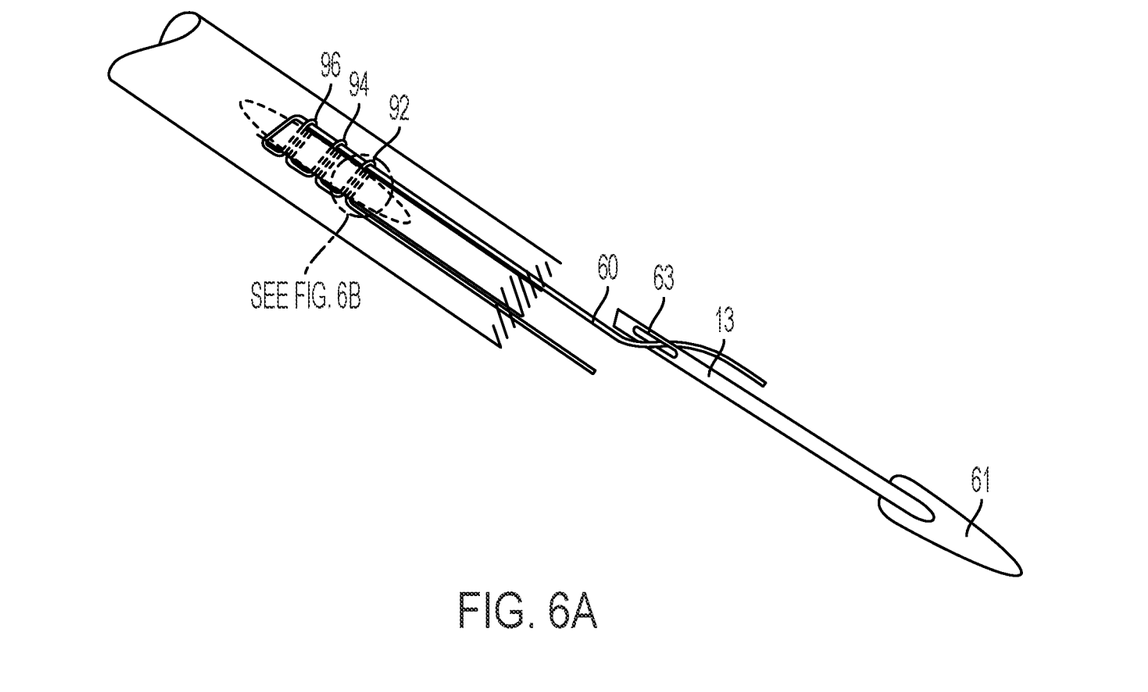
FIGS. 6A and 6B is a schematic illustration depicting the manner in which a suture is weaved through an Achilles tendon using the needle assembly of FIG. 2B.
Figure 6B:
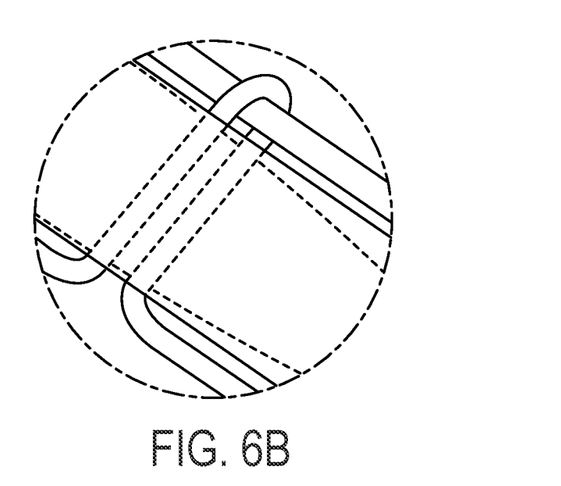

With reference to FIG. 3C, first suture S1 may, for example, enter the proximal end 28 of housing 12 and extend to the base end 70 of needle 16 where it is wrapped around needle 16 in the suture channel thereof, the first suture may then extend to the base end 72 of needle 18 where it is wrapped around needle 18 in the suture channel thereof, the first suture may then extend to the base end 74 of needle 20 where it is wrapped around needle 20 in the suture channel thereof before it connected to a distal end of stylet 13. As a result, when needles 16, 18, 20 pierce the Achilles tendon, first suture S1 is weaved through the tendon as shown in FIG. 6 to form a first suture loop 92, a second suture loop 94, and a third suture loop 96.

Suture loops 92, 94, 96 are formed behind the interior face of the deployment wall 40 and in needle receiving slots 50, 52, 54. Cinching suture 60 (e.g., the portion of the suture S1 located between the third suture loop and stylet 13) may then be pulled through the first, second and third suture loops 92, 94, 96 for cinching first suture S1 to the tendon.

FIGS. 4, 5A, 5B illustrate exemplary needle assemblies. As shown, each of these needle assemblies include needles 16, 18, 20. However, it will be appreciated that either needle assembly may include any number of needles including fewer than three needles or more than three needles. In an embodiment, in which the needle assembly only includes needles 16, 18, the needles have arc length L1, L2. In embodiments in which the needle assembly includes three or more needles, two or more of the needles may have the same or different arc lengths, for example, L1, L1, L2. Moreover, although the needle assemblies illustrated in FIGS. 4, 5A, 5B, have arc lengths L1, L2, L3 that increase in length from the proximal end of shaft 14 to the distal end of the shaft, it will be appreciated that the arc lengths of each of the needles need not be in an ascending order, for example, needle 16 may have an arc length L2, needle 18 may have an arc length L1, and needle 20 may have an arc length L3, so long as the needles enter gap 42 simultaneously (i.e., at least one needle enters the gap at a different time than at least one of the other needles).

With specific reference to FIGS. 4A-4D, needle tips 76, 78, 80 include a single prong 98. Prong 98 may extend from a lateral edge of needles 16, 18, 20 and have a tetrahedron or pyramid shape. Prong 98 includes a first lateral edge 99 that is substantially flush with the lateral edge of the needle from which it extends and a second lateral edge 100 that tapers toward an opposing lateral edge of the needle in front of suture channel 88. Thus, when needles 16, 18, 20 pierce a tendon, lateral edge 100 diverts tissue away from suture channel 88 and shields the suture channel, preventing the suture channel from being clogged.

With specific reference to FIG. 5A and 5B, illustrating a different needle assembly, needle tips 76, 78, 80 include a dual pronged tip 102 such that each one of the prongs is positioned on a lateral side of suture channel 88. Prong 102 may be tapered from the inner circumferential edge 84 of needles 16, 18, 20 toward outer the circumferential edge 90 of the needles to reduce trauma during piercing of the Achilles tendon.

Figure 7A:
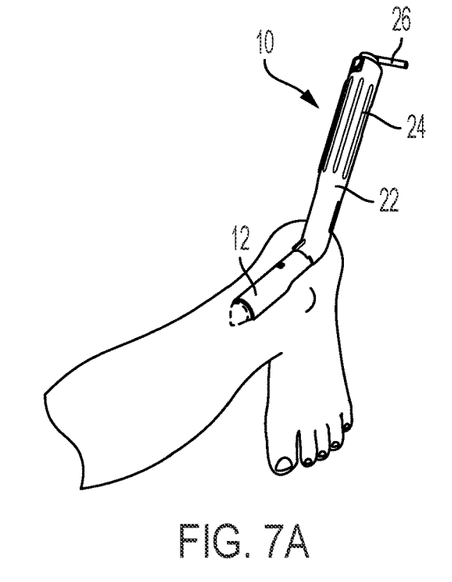
FIGS. 7A-7E are schematic views showing the use of the suture delivery device of FIG. 2B for attaching one or more sutures to first and second Achilles tendon portions and securement of the first and second portions to one another.

With reference to FIGS. 7A-7E, use of tissue repair device 10 will now be described. A surgeon may introduce housing 12 into a single incision located in the posterior region of a patient's leg, superior to the foot and in proximity to a ruptured or damaged Achilles tendon. As shown in FIG. 7A, which illustrates a posterior view of a ruptured tendon, housing 12 may be introduced through a single, small incision, for example, 3 cm in length. The incision may be in proximity to the rupture, inferior to the first Achilles tendon portion AT1 and superior to the second Achilles tendon portion AT2. Because handle 22 is angled relative to housing 12, grip 24 may be angled away from the patient's foot and remain freely operable without interference.

Once housing 12 has been introduced through the incision, a first portion of the ruptured Achilles tendon AT1 may be may be slid through the opening 32 of the housing and positioned at least partially in gap 42. Once suitably positioned, actuator 26 may be rotated or otherwise actuated to rotate shaft 14, causing needles 16, 18, 20 to simultaneously articulate. Because needles 16, 18, 20 are mounted along an axis extending parallel to the longitudinal axis L of housing 12 and have arc lengths L1, L2, L3, respectively, needle tips 76, 78, 80 will pierce and pass through the first portion of the Achilles tendon AT1 in a sequential order. More specifically, needle tip 80 first pierces the first portion of the Achilles tendon at a first location, needle tip 78 then pierces the first portion of the Achilles tendon at a second location, and needle tip 76 will then pierce the first portion of the Achilles tendon at a third location. The sequential piercing of the Achilles tendon reduces trauma on the Achilles tendon.

After needles 16, 18, 20 have articulated through the first Achilles tendon portion AT1 to the deployed position, needle tips 76, 78, 80 are positioned in corresponding needle receiving slots 50, 52, 54 as described above and illustrated in FIG. 3D. At this time, notches 82 of needles 16, 18, 20 are aligned with stylet channel 56 and first suture Si has been passed through the Achilles tendon as shown in FIG. 4 forming suture loops 92, 94, 96.

Figure 7B:
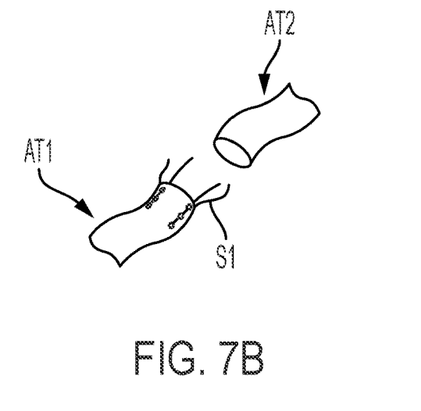

A user may then push stylet 13 through locking channel 56 (from the position shown in FIG. 3C to the position shown in FIG. 3D). After tip 61 has emerged from locking channel 56, the user may pull the tip in the proximal direction to pull a rear end of stylet 13 through transition section 60 and locking channel 59. This, in turn, passes cinching suture 60 through suture loops 92, 94, 96, as illustrated in FIG. 7B and causes suture Si to slide off of needles 16, 18, 20 as the suture is tensioned over its entire length and to the first portion of the Achilles tendon AT1. Each one of needles 16, 18, 20 may then be retracted to their pre-deployment positions, for example, by actuating actuator 26 in a reverse direction.

Figure 7C:
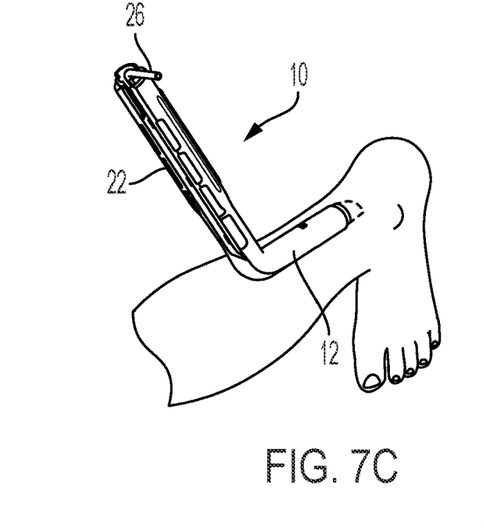
Figure 7D:
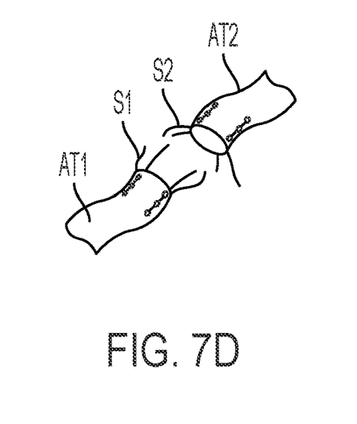
Figure 7E:
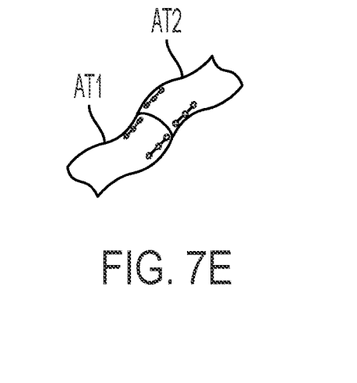

With the first portion of Achilles tendon AT1 secured, the tissue repair assembly 10 may then be removed from the incision and the same tissue repair device 10 (or a second device) with a second suture S2 may be re-introduced through the same incision in the opposing direction. The second portion of the Achilles tendon AT2 may then be positioned within the gap 42 of housing 12 as shown in FIG. 7C. The suture delivery assembly 10 may then again be actuated as described above to secure second suture S2 to the second Achilles tendon portion AT2 as shown in FIG. 7D. Suture delivery assembly 10 may then again be removed and the first and second sutures S1, S2 may be tied to one another to approximate and secure the terminal ends of the first and second Achilles tendon portions AT1, AT2 against one another to facilitate healing as shown in FIG. 7E.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for repairing tissue, comprising:
   positioning a portion of a torn tendon within a tissue receiving gap defined in a housing of a suture delivery assembly; and
   simultaneously actuating first and second needles at least partially through the tissue receiving gap such that the first and second needles respectively pierce the torn tendon at first and second locations,
   wherein the first needle has a first arc length and the second needle has a second arc length different from the first arc length such that the first needle enters the tissue receiving gap before the second needle enters the tissue receiving gap.

2. The method of claim 1, wherein the actuating step comprises rotating a shaft to which the first and second needles are attached.

3. The method of claim 1, wherein the first needle defines a first stylet clearance slot spaced a first distance from a piercing tip of the first needle and the second needle defines a second stylet clearance slot spaced a second distance from a piercing tip of the second needle, the first distance being greater than the second distance.

4. The method of claim 3, further comprising positioning the first stylet clearance slot and the second stylet clearance slot along a locking channel of the housing such that the first and second stylet clearance slots are longitudinally aligned with one another.

5. The method of claim 4, further comprising passing a suture through the torn tendon at the first location and the second location.

6. The method of claim 5, further comprising advancing a stylet carrying a cinching suture in a longitudinal direction through the suture delivery assembly and through the first stylet clearance slot and the second stylet clearance slot.

7. The method of claim 1, wherein introducing the suture delivery assembly includes introducing the suture delivery assembly through a single incision along a posterior region of a leg.

8. The method of claim 7, further comprising retracting the first needle and the second needle and withdrawing the suture delivery assembly from the incision.

9. The method of claim 1, wherein the torn tendon is the Achilles tendon.

10. A method for repairing tissue, comprising:
    positioning a first portion of a torn tendon within a tissue receiving gap defined in a housing of a suture delivery assembly; and
    simultaneously actuating first, second and third needles at least partially through the tissue receiving gap, wherein the first needle has a first arc length, the second needle has a second arc length and the third needle has a third arc length, the first, second and third arc lengths being different from each other, such that the first, second and third needles consecutively pierce the first portion of the torn tendon at first, second and third locations, respectively; and
    advancing a stylet through the suture delivery assembly and through first, second and third stylet clearance slots defined in the first, second and third needles, respectively.

11. The method of claim 10, wherein the actuating step comprises rotating a shaft to which the first, second and third needles are attached.

12. The method of claim 10, wherein the first stylet clearance slot is spaced a first distance from a piercing tip of the first needle, the second stylet clearance slot is spaced a second distance from a piercing tip of the second needle and the third stylet clearance slot is spaced a third distance from a piercing tip of the third needle, and wherein the first distance is greater than the second distance, and the second distance is greater than the third distance.

13. The method of claim 12, further comprising positioning the first, second and third stylet clearance slots along a locking channel of the housing such that the first, second and third stylet clearance slots are longitudinally aligned with one another.

14. The method of claim 13, further comprising passing a suture through the first portion of the torn tendon at the first, second and third locations.

15. The method of claim 10, wherein introducing the suture delivery assembly includes introducing the suture delivery assembly through an incision along a posterior region of a leg.

16. The method of claim 10, further comprising retracting the first, second and third needles and withdrawing the suture delivery assembly from the incision.

17. The method of claim 16, further comprising:
positioning a second portion of a torn tendon within the tissue receiving gap defined in the housing of the suture delivery assembly; and
simultaneously actuating the first, second and third needles at least partially through the tissue receiving gap such that the first, second and third needles consecutively pierce the second portion of the torn tendon at first, second and third locations, respectively; and
advancing the stylet through the suture delivery assembly and through the first, second and third first stylet clearance slots defined in the first, second and third needles.

18. The method of claim 17, further comprising retracting the first, second and third needles and withdrawing the suture delivery assembly from the incision.

19. The method of claim 18, further comprising securing a first suture passed through the first portion of the torn tendon to a second suture passed through the second portion of the torn tendon.

20. The method of claim 10, wherein the torn tendon is the Achilles tendon.

\* \* \* \* \*